United States Patent
Weser et al.

(10) Patent No.: US 9,186,309 B2
(45) Date of Patent: *Nov. 17, 2015

(54) SUBSTANCE FOR DYEING KERATIN FIBERS, INCLUDING CATIONIC ANTHRAQUINONE DYES AND FATTY ACID DIESTERS OF ALKANE DIOLS

(71) Applicant: Henkel AG & Co. KGaA, Düsseldorf (DE)

(72) Inventors: Gabriele Weser, Neuss (DE); Claudia Kolonko, Remscheid (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/310,708

(22) Filed: Jun. 20, 2014

(65) Prior Publication Data

US 2014/0298597 A1  Oct. 9, 2014

Related U.S. Application Data

(63) Continuation of application No. PCT/EP2012/072477, filed on Nov. 13, 2012.

(30) Foreign Application Priority Data

Dec. 20, 2011 (DE) .......... 10 2011 089 222

(51) Int. Cl.
- *A61Q 5/10* (2006.01)
- *A61K 8/41* (2006.01)
- *A61K 8/35* (2006.01)
- *A61K 8/37* (2006.01)
- *A61Q 5/06* (2006.01)

(52) U.S. Cl.
CPC ................. *A61K 8/416* (2013.01); *A61K 8/355* (2013.01); *A61K 8/375* (2013.01); *A61Q 5/065* (2013.01); *A61Q 5/10* (2013.01); *A61K 2800/4322* (2013.01)

(58) Field of Classification Search
CPC ........... A61Q 5/10; A61Q 5/065; C09B 1/207
USPC ...................... 8/405, 552, 582, 643
See application file for complete search history.

(56) References Cited

U.S. PATENT DOCUMENTS

| 5,520,707 A | 5/1996 | Lim et al. |
| 2008/0189876 A1* | 8/2008 | Trigg et al. ............... 8/405 |

FOREIGN PATENT DOCUMENTS

| CA | 2613049 | * | 11/2007 |
| CA | 2613049 A1 | | 4/2008 |
| DE | 102008036957 A1 | | 2/2010 |
| DE | 102009054569 | * | 10/2010 |
| EP | 1006154 B1 | | 6/2000 |
| EP | 1820826 A1 | * | 8/2007 |
| EP | 2272492 A1 | | 1/2011 |
| EP | 2329809 A1 | | 6/2011 |
| WO | 0176552 A2 | | 10/2001 |

OTHER PUBLICATIONS

STIC Search Report dated Aug. 23, 2014.*
English translation (Sep. 9, 2014) of the Patent DE 102009054569.*
KH. Schrader: 'Grundlagen und Rezepturen der Kosmetika', (translation Basics and recipes of cosmetics), 2., verbesserte und erweiterte Auflage, 1989, Huthig Buch Verlag Heidelberg, pjs 1-20 (book table of contents), English abstract machine translation only.

* cited by examiner

*Primary Examiner* — Eisa Elhilo
(74) *Attorney, Agent, or Firm* — Steven L. Nichols; Fabian VanCott

(57) ABSTRACT

The present disclosure provides an agent for coloring keratinic fibers comprising, in a cosmetic carrier, (a) at least one compound of formula (I), and (b) at least one fatty acid diester of an alkanediol. The present disclosure also provides a method of using such an agent to produce increased shine, an intense color result with improved fastness properties, or reduced selectivity.

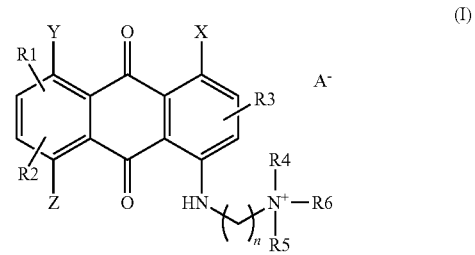

(I)

20 Claims, No Drawings though intense colors with good fastness properties may be obtained with oxidation dyes, the development of the color generally takes place under the influence of oxidizing agents such as $H_2O_2$, for example, which in some cases may result in damage to the fiber. Furthermore, some oxidation dye precursors or certain mixtures of oxidation dye precursors may have a sensitizing effect on people with sensitive skin. Substantive dyes are applied under gentler conditions. The disadvantage of these dyes, however, lies in the fact that the colors often have inadequate fastness properties, in particular with regard to hair washing, but also with respect to external influences, such as sunlight, or reactive environmental chemicals, such as, for example, swimming pool water.

SUBSTANCE FOR DYEING KERATIN FIBERS, INCLUDING CATIONIC ANTHRAQUINONE DYES AND FATTY ACID DIESTERS OF ALKANE DIOLS

RELATED DOCUMENTS

The present application claims the benefit and is a U.S. continuation patent application under 35 U.S.C. 111(a) and claims the right of priority under 35 U.S.C. 365 to international patent Application No. PCT/EP2012/072477, filed Nov. 13, 2012, entitled "SUBSTANCE FOR DYEING KERATIN FIBERS, CONTAINING CATIONIC ANTHRAQUINONE DYES AND FATTY ACID DIESTERS OF ALKANE DIOLS" which claims benefit of German application No.: 102011089222.2, filed Dec. 20, 2011, these applications are herein incorporated by reference in their entirety.

FIELD OF THE INVENTION

The present specification relates generally to agents for coloring and optionally simultaneously lightening keratinic fibers. More specifically, the present application relates to cosmetic agents including cationic anthraquinone dyes and special fatty acid diesters of alkanediols. The present application also relates to the use of these agents to produce hair colors having increased shine, an intense color result, improved fastness properties and reduced selectivity.

BACKGROUND OF THE INVENTION

As a general rule, either substantive dyes or oxidation dyes may be used for coloring keratinic fibers. Al- For temporary colors, coloring or tinting agents may be used which include substantive dyes as the coloring component. These are dye molecules which attach directly to the hair and do not require an oxidative process to develop the color. These colors are generally significantly more sensitive to shampooing than oxidative colors, such that an often undesired shift in shade or even a visible "decolorization" occurs much more quickly.

Achieving a uniform coloring of hair that has been frequently treated, such as for example bleached or permanently waved hair, where the fibers present differing degrees of pre-existing damage in the various lengths or variously treated areas, represents a particular challenge in terms of coloring hair with substantive dyes. During the coloring process itself, the coloring agent may exhibit uneven coloring on hair with differing degrees of pre-existing damage, while repeated hair washing may also cause the dyes to be washed out of the different areas of the hair to varying degrees, resulting in an inconsistent, and hence undesirable, color result.

In the development of coloring products based on substantive dyes, there is still a particular focus on producing dye formulations having reduced selectivity, meaning that a uniform color result may be achieved on sections of the hair that have varying degrees of pre-existing damage. In particular, this reduced selectivity should remain present not only immediately after the coloring process but also after repeated hair washes.

Formulations including surfactants are often used for coloring keratinic fibers. The use of surfactants has the disadvantage that too great a degreasing of the scalp may occur during the hair coloring process, leading to an itchy scalp or to the formation of dandruff. Oil-replenishing substances which preserve the lipid content of the scalp may be used in the hair coloring formulations to protect the scalp. However, oil-replenishing substances which have a positive effect on the scalp may lead to a negative effect on the hair fiber, since the oil-replenishing substances cause the hair to appear greasy too quickly, giving an unkempt and unattractive appearance to the hairstyle. Despite the large number of active ingredients that are now known in the industry, there is therefore still a need for substances or combinations of substances which protect the scalp during the coloring process and give the hair shine, without making it appear prematurely greasy.

In addition, the use of some active ingredients may be incompatible with the dyes that are used, such that the color result obtained with a combination of an active ingredient and dye is poorer than that obtained with the dye alone. There is, therefore, a need for suitable combinations of active ingredients and dyes, in which the positive effect of the active ingredient may develop without also having a disadvantageous effect on the fastness properties of the dye.

An object of the present specification is therefore to provide a coloring agent for keratinic fibers, in particular human hair, which, in addition to other positive fastness properties, has a low selectivity (or a good equalizing capacity) and good wash fastness. At the same time, the scalp should be protected during the coloring process and a shine should be imparted to the keratinic fibers, without however making them appear prematurely greasy.

The use of cationic anthraquinone dyes in products for coloring keratinic fibers is already known in principle from the prior art, for example from EP 1 006 154 B1 or EP 1 820 826 A1. Furthermore, combinations of cationic anthraquinone dyes with oxidation dye precursors of the developer type are claimed in EP 2 329 809 for the oxidative coloring of hair.

Combinations of cationic anthraquinones with special fatty acid diesters of an alkanediol have not yet been described. During the course of the work leading to the agents of this disclosure, it was surprisingly found that these combinations lead to colors which achieve the above object to an outstanding degree.

Furthermore, other desirable features and characteristics of the present invention will become apparent from the subsequent detailed description of the invention and the appended claims, taken in conjunction with this background of the invention.

BRIEF SUMMARY OF THE INVENTION

The present specification firstly provides an agent for coloring (which may also simultaneously lighten) keratinic fibers comprising, in a cosmetic carrier, (a) at least one compound of formula (I):

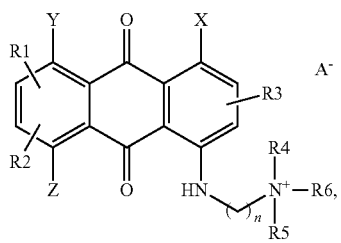

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
  or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen, a hydroxyl group or an N(R7)(R8) group,
  in which:
    R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;
n denotes an integer between 2 and 6 inclusive; and
$A^-$ denotes a physiologically acceptable anion;
and
(b) at least one fatty acid diester of an alkanediol.

The present specification secondly provides a method of using a cosmetic agent for coloring keratinic fibers. The method comprises:
(A) applying an agent for coloring (which may also simultaneously lighten) keratinic fibers comprising, in a cosmetic carrier,
(i) at least one compound of formula (I):

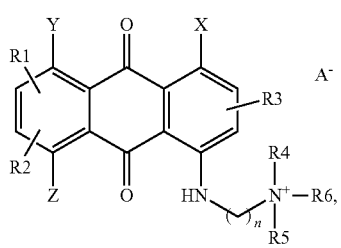

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
  or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen, a hydroxyl group or an N(R7)(R8) group,
  in which:
    R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;
n denotes an integer between 2 and 6 inclusive; and
$A^-$ denotes a physiologically acceptable anion;
and
(ii) at least one fatty acid diester of an alkanediol; and
(B) after a contact time, rinsing the agent from the keratinic fibers.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

According to the present specification, the terms "keratin-containing fibers," "keratinic fibers," or similar terminology is understood to mean all animal hair, for example wool, horsehair, angora hair, fur, feathers and products or textiles manufactured therefrom. The keratinic fibers are, however, preferably human hair.

The term "coloring of keratin fibers," in the context of the present specification to includes any form of changing the color of keratin fibers. It includes in particular the color changes covered by the terms tinting, lightening, bleaching, peroxiding, oxidative coloring, semipermanent coloring, permanent coloring and temporary coloring. It explicitly also includes color changes according to the present specification, presenting a lighter color result in comparison to the original color, such as for example, combined coloring and bleaching processes.

The agents according to the present specification include the cationic anthraquinone(s) of formula (I) and the fatty acid diester(s) of alkanediols in a cosmetic carrier, preferably in a suitable aqueous, alcoholic or aqueous-alcoholic carrier. For the purposes of hair coloring, such carriers are for example creams, emulsions, gels or surfactant-containing foaming solutions, such as for example shampoos, foam aerosols, foam formulations or other preparations which are suitable for use on the hair. It is also possible, however, for the agents according to the present specification to be integrated into a formulation in powder or tablet form.

Within the meaning of the present specification, aqueous-alcoholic solutions are understood to be aqueous solutions including 3 to 70 weight percent (wt. %) of a $C_1$ to $C_4$ alcohol, in particular ethanol or isopropanol. The agents according to the present specification may additionally include further organic solvents, such as for example methoxybutanol, benzyl alcohol, ethyl diglycol or 1,2-propylene glycol. All water-soluble organic solvents are preferred here.

The first essential ingredient (a) of the agents according to the present specification is at least one substantive cationic anthraquinone dye of the general formula (I):

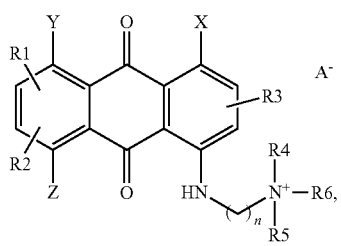

The substituents R1 to R8 of the compound of formula (I) are described below by way of non-limiting examples: Examples of a $C_1$-$C_6$ alkyl group are the methyl, ethyl, propyl, isopropyl, n-butyl, s-butyl and t-butyl, n-pentyl and n-hexyl groups. Propyl, ethyl and methyl are preferred alkyl residues. Examples of a $C_2$-$C_6$ alkenyl group are vinyl, allyl, but-2-enyl, but-3-enyl and isobutenyl, preferred $C_2$-$C_6$ alkenyl residues being vinyl and allyl. Preferred examples of a $C_1$-$C_6$ hydroxyalkyl group are a hydroxymethyl, 2-hydroxyethyl, 2-hydroxypropyl, 3-hydroxypropyl, 4-hydroxybutyl, 5-hydroxypentyl and 6-hydroxyhexyl group; a 2-hydroxyethyl group is particularly preferred. $C_1$-$C_6$ alkoxy groups that are preferred according to the present specification are the methoxy or ethoxy group. Examples of halogen atoms are F, Cl, Br or I atoms, with Br or Cl atoms being most particularly preferred. Preferred examples of $C_1$-$C_6$ alkoxy $C_2$-$C_6$ alkyl groups are the methoxyethyl, ethoxyethyl, methoxypropyl, methoxybutyl, ethoxypropyl, ethoxybutyl and methoxyhexyl group. Examples of a $C_1$-$C_6$ acyl amino group are the acetamide group, the propanamide group and the butanamide group, the acetamide group being preferred. The pyrrolidinium ring, the piperidinium ring, the morpholinium ring and the 1-azepanium ring may be mentioned as preferred examples of a 5-, 6- or 7-membered ring formed from R4, R5 and the quaternary nitrogen atom.

Dyes of formula (I) in which R1, R2 and R3, independently of one another, denote hydrogen, halogen, a carboxyl group, a sulfonic acid group, a $C_1$-$C_6$ alkyl group or a $C_1$-$C_6$ alkoxy group deliver particularly intense color results and are therefore preferred.

It is furthermore preferable for one of the residues selected from R1, R2 and R3 to denote halogen, a carboxyl group, a sulfonic acid group, a $C_1$-$C_6$ alkyl group or a $C_1$-$C_6$ alkoxy group and for the other two residues selected from R1, R2 and R3 both to denote hydrogen.

A preferred example is an agent for coloring, and optionally simultaneously lightening, keratinic fibers, which is characterized in that it includes a compound of formula (I) in which at least one of the residues R1, R2 and/or R3 denotes a $C_1$-$C_6$ alkyl group.

In the case of particularly suitable compounds of formula (I), one of the residues selected from R1, R2 and R3 denotes a $C_1$-$C_6$ alkyl group and the other two residues selected from R1, R2 and R3 denote hydrogen.

In a most particularly preferred example, R1 and R2 both denote a hydrogen atom and R3 denotes a methyl group.

Furthermore, particularly good coloring results are obtained with agents including at least one compound of formula (I) in which the residues R4, R5 and R6, independently of one another, denote a $C_1$-$C_6$ alkyl group or an alkenyl group. In particular, each of the residues R4, R5 and R6 preferably denotes a $C_1$-$C_6$ alkyl group.

It is most particularly preferable for R4 and R5 both to denote a methyl group and for R6 to denote a methyl group, an ethyl group or an n-propyl group.

It is moreover most particularly preferable for R4 and R5 both to denote a methyl group and for R6 to denote an n-propyl group.

In a likewise particularly preferred example the residues R4, R5 and R6 each denote a methyl group.

For compounds of formula (I) there is the proviso that at least one of the residues X, Y and Z denotes an N(R7)(R8) group. Colors having good application properties were obtained in particular when compounds of formula (I) were used in which X denotes an N(R7)(R8) group and Y and Z each denote hydrogen.

R7 and R8, preferably (and independently of one another) denote hydrogen or a $C_1$-$C_6$ alkyl group. R7 and R8 particularly preferably (also independently of one another) denote hydrogen or a methyl group. Compounds of formula (I) in which both R7 and R8 denote hydrogen have proved to be particularly suitable and are therefore particularly preferred.

In the context of the work leading to the agents of this disclosure it has proved most particularly advantageous for X to denote an $NH_2$ group.

A further preferred example is therefore an agent for coloring, and optionally simultaneously lightening, keratinic fibers, which is characterized in that it includes a compound of formula (I) in which at least X denotes an $NH_2$ group.

n preferably denotes the numbers 2 or 3 and most particularly preferably the number 3.

$A^-$ denotes a physiologically acceptable anion. Suitable physiologically acceptable anions are halide, hydrogen sulfate, ½ sulfate, benzene sulfonate, p-toluenesulfonate, acetate, citrate, lactate, ½ tartrate, methosulfate ($H_3COSO_3^-$) or trifluoromethane sulfonate. K particularly preferably denotes bromide or methosulfate ($H_3COSO_3^-$), with K most particularly preferably denoting methosulfate ($H_3COSO_3^-$).

Agents for coloring, and optionally simultaneously lightening, keratinic fibers that are preferred according to the present specification are characterized in that they include at least one compound of the general formula (I) selected from 3-[(4-amino-9,10-dihydro-3-methyl-9,10-dioxo-1-anthracenyl)amino]-N,N,N-trimethyl-1-propanaminium methosulfate, 3-[(4-amino-9,10-dihydro-3-methyl-9,10-dioxo-1-anthracenyl)amino]-N,N,N-trimethyl-1-propanaminium bromide, 3-[(4-amino-9,10-dihydro-3-methyl-9,10-dioxo-1-anthracenyl)amino]-N,N,N-trimethyl-1-propanaminium chloride, 3-[(4-amino-9,10-dihydro-3-methyl-9,10-dioxo-1-anthracenyl)amino]-N,N,N-trimethyl-1-propanaminium-p-toluenesulfonate, 3-[(4-amino-9,10-dihydro-3-methyl-9,10-dioxo-1-anthracenyl)amino]-N,N,N-trimethyl-1-propanaminium acetate, 3-{[9,10-dihydro-4-(methylamino)-9,10-dioxo-1-anthracenyl]amino}-N,N-dimethyl-N-propyl-1-propanaminium methosulfate, 3-{[9,10-dihydro-4-(methylamino)-9,10-dioxo-1-anthracenyl]amino}-N,N-dimethyl-N-propyl-1-propanaminium bromide, 3-{[9,10-dihydro-4-(methylamino)-9,10-dioxo-1-anthracenyl]amino}-N,N-dimethyl-N-propyl-1-propanaminium chloride, 3-{[9,10-dihydro-4-(methylamino)-9,10-dioxo-1-anthracenyl]amino}-N,N-dimethyl-N-propyl-1-propanaminium-p-toluenesulfonate and 3-{[9,10-dihydro-4-(methylamino)-9,10-dioxo-1-anthracenyl]amino}-N,N-dimethyl-N-propyl-1-propanaminium acetate.

The compound of formula (Ia) has proved to be an ideally suitable compound of formula (I) for achieving the object according to the present specification

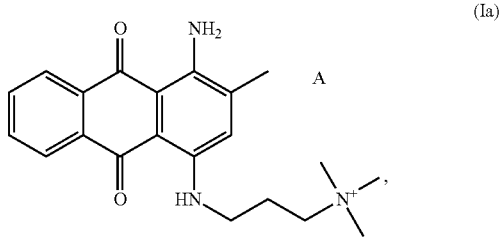

in which A⁻ denotes a physiologically acceptable anion, preferably methosulfate ($H_3COSO_3^-$).

A further particularly preferred example is therefore an agent for coloring and optionally simultaneously lightening keratinic fibers, which is characterized in that it includes as the compound of formula (I) the compound according to formula (Ia),

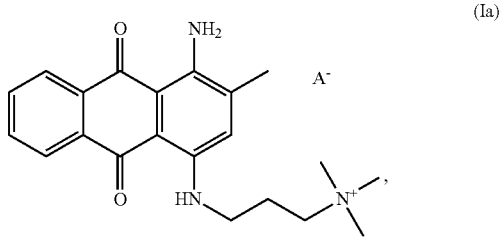

in which A⁻ denotes a physiologically acceptable anion, preferably methosulfate ($H_3COSO_3^-$).

The agents according to the present specification for coloring, and optionally simultaneously lightening, keratin fibers include the compound(s) of formula (I) preferably in amounts above 0.0001 wt. % and below 5 wt. %, relative in each case to the total agent.

A preferred example is an agent which includes the compound(s) of formula (I) in an amount of from 0.0001 to 5 wt. %, preferably from 0.005 to 3.5 wt. %, particularly preferably from 0.01 to 2.5 wt. %, in particular from 0.05 to 1.5 wt. %, and in particular preferably from 0.01 to 1.0 wt. %, relative in each case to the total weight of the agent.

As the second essential constituent of the formulation (b), the agents according to the present specification include at least one fatty acid diester of an alkanediol.

Within the meaning of the present specification a fatty acid diester of an alkanediol is understood to be an alkanediol in which both hydroxyl groups are esterified with a fatty acid.

The alkanediol may be esterified with either two identical fatty acids or with two different fatty acids.

According to the present specification fatty acids are understood to be saturated or unsaturated, unbranched or branched, unsubstituted or substituted $C_8$-$C_{24}$ carboxylic acids. Unsaturated fatty acids may be mono- or polyunsaturated. In the case of an unsaturated fatty acid the C—C double bond(s) thereof may have either the cis- or trans-configuration.

Within the context of the present specification, alkanediols are understood to be alkyl chains, in particular $C_2$-$C_{10}$ alkyl chains, bearing two hydroxyl groups. The two hydroxyl groups are located on different carbon atoms of the $C_2$-$C_{10}$ alkyl chain. In addition to the two hydroxyl groups the $C_2$-$C_{10}$ alkyl chains may also bear further substituents. It is preferable, however, for there to be no further substituents present in the $C_2$-$C_{10}$ alkyl chains other than the two hydroxyl groups. 1,2-Alkanediols and 1,3-alkanediols are preferred.

Ethylene glycol and/or propylene glycol which have been esterified with fatty acids are particularly preferably used in the agents according to the present specification as fatty acid diesters of an alkanediol (b).

Particularly suitable representatives of fatty acid diesters of an alkanediol (b) are encompassed by formula (II):

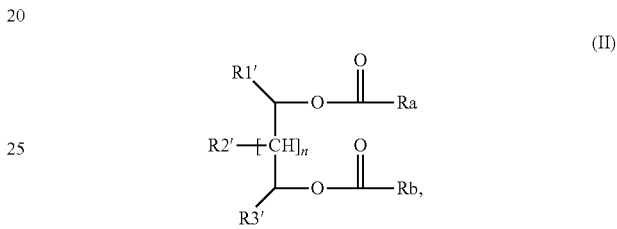

in which:
R1', R3' independently of one another, denote hydrogen, a $C_1$-$C_8$ alkyl group, an aryl group or a hydroxy-$C_1$-$C_6$ alkyl group,
R2' denotes hydrogen, a hydroxyl group, a $C_1$-$C_8$ alkyl group, an aryl group or a hydroxy-$C_1$-$C_6$ alkyl group,
n denotes an integer from 0 to 8 (inclusive), and
Ra, Rb independently of one another, denote a saturated or unsaturated, unbranched or branched, unsubstituted or substituted $C_7$-$C_{23}$ alkyl group.

R1' and R3' preferably (and independently of one another) denote hydrogen, a $C_1$-$C_8$ alkyl group or a hydroxy-$C_1$-$C_6$ alkyl group. Particularly preferable are hydrogen or a methyl group.

It is moreover preferable for R2' to denote hydrogen, a hydroxyl group or a $C_1$-$C_8$ alkyl group. In particular, R2' preferably denotes hydrogen. n preferably denotes 0 or 1. n particularly preferably denotes 0.

Examples of suitable fatty acid diesters of an alkanediol (b) include compounds wherein at least one of the ester groups is formed starting from the alkanediol with a saturated fatty acid. In this context a fatty acid selected from the following is preferably used as the saturated fatty acid:

TABLE 1

Exemplary F groups which may provide Ra and/or Rb.

| | Fatty acid | Ra and/or Rb = |
|---|---|---|
| F1 | Octanoic acid (caprylic acid) | —$C_7H_{15}$ |
| F2 | Decanoic acid (capric acid) | —$C_9H_{19}$ |
| F3 | Dodecanoic acid (lauric acid) | —$C_{11}H_{23}$ |
| F4 | Tetradecanoic acid (myristic acid) | —$C_{13}H_{27}$ |
| F5 | Hexadecanoic acid (palmitic acid) | —$C_{15}H_{31}$ |
| F6 | Octadecanoic acid (stearic acid) | —$C_{17}H_{35}$ |
| F7 | Eicosanoic acid (arachidic acid) | —$C_{19}H_{39}$ |
| F8 | Docosanoic acid (behenic acid) | —$C_{21}H_{43}$ |
| F9 | Tetracosanoic acid (lignoceric acid) | —$C_{23}H_{47}$ |

Within this example it is particularly advantageous if the agent includes a fatty acid diester of an alkanediol (b) in which at least one ester bond is formed with a saturated $C_{14}$-$C_{20}$ fatty acid.

Particularly preferred compounds of the general formula (II) are thus compounds in which at least one of the residues Ra and/or Rb denotes a saturated, unbranched or branched, unsubstituted or substituted $C_{13}$-$C_{19}$ alkyl group.

Compounds of formula (II) in which at least one of the residues selected from Ra and/or Rb denotes the residue —$C_{13}H_{27}$ (F4), —$C_{15}H_{31}$ (F5), —$C_{17}H_{35}$ (F6) and/or —$C_{19}H_{39}$ (F7) are most particularly suitable.

The fatty acid triglycerides in which at least one of the ester groups is formed starting from the alkanediol with a mono- or polyunsaturated fatty acid are also very suitable. A fatty acid selected from the following is preferably used as the unsaturated fatty acid:

agent to include at least one fatty acid diester of an alkanediol (b) in which at least one ester bond of the alkanediol is formed with a mono-, di- or tri-unsaturated $C_{16}$-$C_{20}$ fatty acid. It is preferable in particular for at least one of the fatty acids selected from palmitoleic acid (F12), oleic acid (F13), linoleic acid (F16) and/or linolenic acid (F17) to be esterified with an alkanediol.

The compounds of formula (II) in which at least one of the residues Ra and/or Rb denotes one of the residues F12, F13, F16 and/or F17 have thus also proved to be particularly advantageous.

The fatty acids that are esterified onto the diol to form the fatty acid diesters of an alkanediol (b) may also bear one or more substituents. Substituted fatty acids preferably bear one or more substituents selected from a hydroxyl group, a carbonyl group and a $C_1$-$C_6$ alkoxy group. The fatty acids are preferably substituted with a hydroxyl group or a methoxy

TABLE 2

Further exemplary F groups which may provide Ra and/or Rb.

| | Fatty acid | Ra and/or Rb = |
|---|---|---|
| F11 | Petroselic acid [(Z)-6-octadecenoic acid] | |
| F12 | Palmitoleic acid [(9Z)-hexadec-9-enoic acid] | |
| F13 | Oleic acid [(9Z)-octadec-9-enoic acid] | |
| F14 | Elaidic acid [(9E)-octadec-9-enoic acid] | |
| F15 | Erucic acid [(13Z)-docos-13-enoic acid] | |
| F16 | Linoleic acid [(9Z,12Z)-octadeca-9,12-dienoic acid | |
| F17 | Linolenic acid [(9Z,12Z,15Z)-octadeca-9,12,15-trienoic acid] | |
| F18 | Elaeostearic acid [(9Z,11E,13E)-octadeca-9,11,13-trienoic acid] | |
| F19 | Arachidonic acid [(5Z,8Z,11Z,14Z)-eicosa-5,8,11,14-tetraenoic acid] | |
| F20 | Nervonic acid [(15Z)-tetracos-15-enoic acid] | |

During the course of the work leading to the agents of this disclosure it also proved to be preferable for the coloring group. A fatty acid selected from the following is preferably used as the substituted fatty acid:

TABLE 3

Additional exemplary F groups which may provide Ra and/or Rb.

| | Fatty acid | Ra and/or Rb = |
|---|---|---|
| F21 | Ricinoleic acid [(12-hydroxy-(Z)-octadec-9-enoic acid | OH |

TABLE 3-continued

Additional exemplary F groups which may provide Ra and/or Rb.

| | Fatty acid | Ra and/or Rb = |
|---|---|---|
| F22 | 12-Hydroxy-octadecanoic acid | 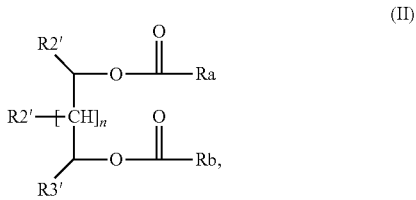 |

Compounds of formula (II) in which at least one of the residues Ra and/or Rb denotes one of the residues F21 or F22 are particularly preferred.

A further particularly preferred example is therefore an agent for coloring, and optionally simultaneously lightening, keratinic fibers, which is characterized in that it includes as the fatty acid diester of an alkanediol (b) a compound of formula (II):

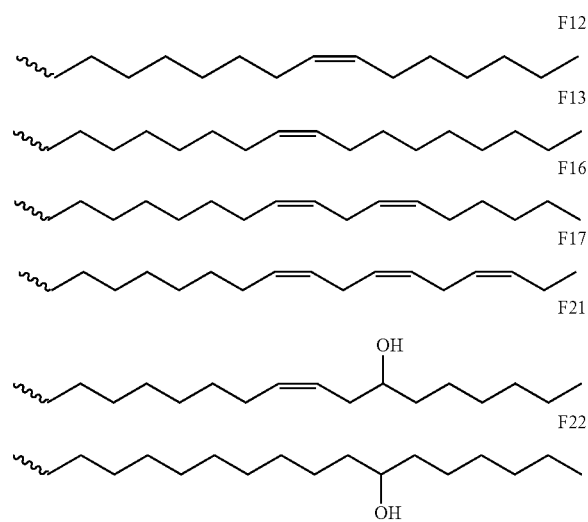

in which:
R1', R3' independently of one another, denote hydrogen, a $C_1$-$C_8$ alkyl group, an aryl group or a hydroxy-$C_1$-$C_6$ alkyl group,
R2' denotes hydrogen, a hydroxyl group, a $C_1$-$C_8$ alkyl group, an aryl group or a hydroxy-$C_1$-$C_6$ alkyl group,
n denotes an integer from 0 to 8 (inclusive), and
Ra, Rb independently of one another, denote a saturated or unsaturated, unbranched or branched, unsubstituted or substituted $C_7$-$C_{23}$ alkyl group,
wherein Ra and/or Rb are preferably selected from —$C_{13}H_{27}$ (F4), —$C_{15}H_{31}$ (F5), —$C_{17}H_{35}$ (F6), —$C_{19}H_{39}$ (F7) and the residues F12, F13, F16, F17, F21 and F22.

In one example of the present disclosure, the agent includes a fatty acid diester of an alkanediol and two structurally identical fatty acids, wherein R1' and R3' both denote hydrogen and n is equal to 0. The diesters of an alkanediol and two structurally identical fatty acids are preferably selected from compounds of formula (II) in which the residues Ra and Rb are as provided in the following table (wherein the F groups are as described in Tables 1, 2 and 3):

TABLE 4

Derivatives of compounds of formula (II), wherein the diol is ethylene glycol, and the Ra and Rb groups are as defined in the table.

| Derivative of formula (II) | Ra | Rb |
|---|---|---|
| 1 | F1 | F1 |
| 2 | F2 | F2 |
| 3 | F3 | F3 |
| 4 | F4 | F4 |
| 5 | F5 | F5 |
| 6 | F6 | F6 |
| 7 | F7 | F7 |
| 8 | F8 | F8 |
| 9 | F9 | F9 |
| 10 | F10 | F10 |
| 11 | F11 | F11 |
| 12 | F12 | F12 |
| 13 | F13 | F13 |
| 14 | F14 | F14 |
| 15 | F15 | F15 |
| 16 | F16 | F16 |
| 17 | F17 | F17 |
| 18 | F18 | F18 |
| 19 | F19 | F19 |
| 20 | F20 | F20 |
| 21 | F21 | F21 |
| 22 | F22 | F22 |

Colors with particularly good wash fastness and particularly high shine are obtained if Ra and Rb both denote a saturated, unbranched, and unsubstituted $C_{14}$-$C_{20}$ alkyl group, and if Ra and Rb are the same.

A further particularly preferred example is therefore an agent for coloring, and optionally simultaneously lightening, keratinic fibers, which is characterized in that it includes as the fatty acid diester of an alkanediol (b) a compound of formula (II) in which Ra and Rb both denote a saturated, unbranched, and unsubstituted $C_{14}$-$C_{20}$ alkyl group, and Ra and Rb are the same.

In a further example of the present disclosure, the agent according to the present specification includes a fatty acid diester of an alkanediol and two structurally different fatty acids, wherein R1' and R3' both denote hydrogen and n is equal to 0. The preferred compounds of this group are selected from compounds of formula (II) in which the residues Ra and Rb are as provided in the following table (wherein the F groups are as described in Tables 1, 2 and 3):

TABLE 5

Derivatives of compounds of formula (II), wherein the diol is ethylene glycol, and the Ra and Rb groups are as defined in the table.

| Derivative of formula (II) | Ra | Rb |
|---|---|---|
| 23 | F4 | F5 |
| 24 | F4 | F6 |
| 25 | F4 | F7 |
| 26 | F4 | F12 |
| 27 | F4 | F13 |
| 28 | F4 | F16 |
| 29 | F4 | F17 |
| 30 | F4 | F21 |
| 31 | F4 | F22 |
| 32 | F5 | F4 |
| 33 | F5 | F6 |
| 34 | F5 | F7 |
| 35 | F5 | F12 |
| 36 | F5 | F13 |
| 37 | F5 | F16 |
| 38 | F5 | F17 |
| 39 | F5 | F21 |
| 40 | F5 | F22 |
| 41 | F6 | F4 |
| 42 | F6 | F5 |
| 43 | F6 | F7 |
| 44 | F6 | F12 |
| 45 | F6 | F13 |
| 46 | F6 | F16 |
| 47 | F6 | F17 |
| 48 | F6 | F21 |
| 49 | F6 | F22 |
| 50 | F7 | F4 |
| 51 | F7 | F5 |
| 52 | F7 | F6 |
| 53 | F7 | F12 |
| 54 | F7 | F13 |
| 55 | F7 | F16 |
| 56 | F7 | F17 |
| 57 | F7 | F21 |
| 58 | F7 | F22 |
| 59 | F12 | F4 |
| 60 | F12 | F5 |
| 61 | F12 | F6 |
| 62 | F12 | F7 |
| 63 | F12 | F13 |
| 64 | F12 | F16 |
| 65 | F12 | F17 |
| 66 | F12 | F21 |
| 67 | F12 | F22 |
| 68 | F13 | F4 |
| 69 | F13 | F5 |
| 70 | F13 | F6 |
| 71 | F13 | F7 |
| 72 | F13 | F12 |
| 73 | F13 | F16 |
| 74 | F13 | F17 |
| 75 | F13 | F21 |
| 76 | F13 | F22 |
| 77 | F16 | F4 |
| 78 | F16 | F5 |
| 79 | F16 | F6 |
| 80 | F16 | F7 |
| 81 | F16 | F12 |
| 82 | F16 | F13 |
| 83 | F16 | F17 |
| 84 | F16 | F21 |
| 85 | F16 | F22 |
| 86 | F17 | F4 |
| 87 | F17 | F5 |
| 88 | F17 | F6 |
| 89 | F17 | F7 |
| 90 | F17 | F12 |
| 91 | F17 | F13 |
| 92 | F17 | F16 |
| 93 | F17 | F21 |
| 94 | F17 | F22 |
| 95 | F21 | F4 |
| 96 | F21 | F5 |
| 97 | F21 | F6 |
| 98 | F21 | F7 |
| 99 | F21 | F12 |
| 100 | F21 | F13 |
| 101 | F21 | F16 |
| 102 | F21 | F17 |
| 103 | F21 | F22 |
| 104 | F22 | F4 |
| 105 | F22 | F5 |
| 106 | F22 | F6 |
| 107 | F22 | F7 |
| 108 | F22 | F12 |
| 109 | F22 | F13 |
| 110 | F22 | F16 |
| 111 | F22 | F17 |
| 112 | F22 | F21 |

For example, the structure of fatty acid diester no. 112 is composed of ethylene glycol and the fatty acid residues Ra=F22 and Rb=F21, resulting in structure $(II_{112})$. The structures of all further derivatives may be derived in the same manner.

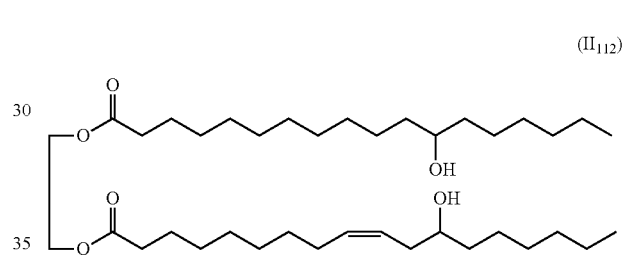

$(II_{112})$

In particular, ethylene glycol distearate (compound $II_6$ in Table 4; INCI name: Ethylene glycol distearate) is preferably used in the agents according to the present specification as the fatty acid diester of an alkanediol (b). This substance is sold for example under the trade names Cutina® AGS, Lipo® EGDS, Loxiol® 2723 and Eumulsan® AGS.

Propylene glycol distearate (INCI name: Propylene glycol distearate, diester of stearic acid with 1,2-propanediol) is also most particularly preferred in this context.

A further particularly preferred example is therefore an agent for coloring, and optionally simultaneously lightening, keratinic fibers, which is characterized in that it includes as the fatty acid diester of an alkanediol (b) ethylene glycol distearate and/or propylene glycol distearate.

The agents according to the present specification for coloring and/or lightening keratinic fibers include the fatty acid diester(s) of an alkanediol (b) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent. The specified proportions by weight relate here to the total amount of all components (b) included in the agent.

A further preferred example is therefore an agent for coloring, and optionally simultaneously lightening, keratinic fibers, which is characterized in that it includes the fatty acid diester(s) of an alkanediol (b) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent.

In a further preferred example the agents according to the present specification additionally include, in addition to the dye of formula (I), at least one further substantive dye. Substantive dyes may be divided into anionic, cationic and non-ionic substantive dyes. The substantive dyes are preferably selected from nitrophenylenediamines, nitroaminophenols, azo dyes, anthraquinones, triarylmethane dyes or indophenols and physiologically acceptable salts thereof. The additional substantive dyes are each preferably used in an amount of from 0.001 to 2 wt. %, relative to the total weight of the agent.

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes including a heterocyclic compound having at least one quaternary nitrogen atom, in particular Basic Yellow 87, Basic Orange 31 and Basic Red 51. The cationic substantive dyes which are sold under the ARIANOR® trademark are likewise preferred cationic substantive dyes according to the present specification.

Non-ionic nitro and quinone dyes and neutral azo dyes in particular are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Coloring results with outstanding color intensity, brilliance and good wash fastness are obtained in particular if the agents according to the present specification include as the further substantive dye at least one dye selected from D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxethyl)-4-methyl-2-nitroaniline (Methyl Yellow), HC Yellow No. 2, Red B 54 and 2-amino-6-chloro-4-phenol.

The agents according to the present specification may moreover also be used as oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are selected from at least one compound from the group formed from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof.

Particularly suitable oxidation dye precursors of the coupler type are selected from the group formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

The substantive dyes, developer components and coupler components are preferably each used in an amount from 0.0001 to 5.0 wt. %, preferably 0.001 to 2.5 wt. %, relative in each case to the ready-to-use agent. Developer components and coupler components may be generally used in approximately molar amounts to one another. Although the molar use has proved convenient, a certain excess of individual oxidation dye precursors is not disadvantageous, such that developer components and coupler components may be in a molar ratio of 1 to 0.5 to 1 to 3, in particular 1 to 1 to 1 to 2.

In the case of oxidation coloring agents, the agents preferably include an oxidizing agent, preferably hydrogen peroxide. The amounts of hydrogen peroxide correspond to the amounts in the lightening agents according to the present specification.

The coloring agents may moreover be used as lightening coloring agents. In order to achieve the lightening effect, the agents include hydrogen peroxide and/or one of the solid addition products thereof with organic or inorganic compounds.

A further example of the first subject matter of the present specification is therefore characterized in that the agent additionally includes hydrogen peroxide and/or one of the solid addition products thereof with organic or inorganic compounds.

In a preferred example, hydrogen peroxide itself is preferably used as an aqueous solution. The concentration of a hydrogen peroxide solution in the agent according to the present specification is determined on the one hand by legal requirements and on the other by the desired effect; 6 to 12 wt. % solutions in water are preferably used. Ready-to-use agents of the first subject matter of the present specification that are preferred according to the present specification are characterized in that they include from 0.5 to 20 wt. %, preferably from 1 to 12.5 wt. %, particularly preferably from 2.5 to 10 wt. % and in particular from 3 to 6 wt. % of hydrogen peroxide, relative in each case to the total weight of the ready-to-use agent.

In order to achieve a stronger lightening and bleaching effect the agent may moreover include at least one peroxo salt. Suitable peroxo salts are inorganic peroxo compounds, preferably selected from the group formed from ammonium peroxodisulfate, alkali metal peroxodisulfates, ammonium peroxomonosulfate, alkali metal peroxomonosulfates, alkali metal peroxodiphosphates and alkaline-earth metal peroxides. Peroxodisulfates are particularly preferred, in particular ammonium peroxodisulfate, potassium peroxodisulfate and sodium peroxodisulfate.

The persulfates may be included in the agent according to the present specification in an amount of from 0.5 to 20 wt. %, preferably from 1 to 12.5 wt. %, particularly preferably from 2.5 to 10 wt. % and in particular from 3 to 6 wt. %, relative in each case to the total weight of the ready-to-use agent.

A further preferred example is an agent for coloring and simultaneously lightening keratinic fibers, which additionally includes hydrogen peroxide, one of the solid addition products thereof with organic or inorganic compounds, ammonium peroxodisulfate, potassium peroxodisulfate and/or sodium peroxodisulfate, each in an amount of from 0.5 to 20 wt. %, preferably from 1 to 12.5 wt. %, particularly preferably from 2.5 to 10 wt. % and in particular from 3 to 6 wt. %, relative to the total weight of the ready-to-use agent.

The ready-to-use coloring agents may moreover include additional active ingredients, auxiliary substances and additives to improve the coloring capacity and to establish further desired properties of the agents.

The ready-to-use coloring agents are preferably provided as a liquid preparation and therefore a surface-active substance is additionally added to the agents, such surface-active substances being referred to as surfactants or emulsifiers, depending on the field of application. They are preferably selected from anionic, cationic, zwitterionic, amphoteric and non-ionic surfactants and emulsifiers.

Agents that are preferred according to the present specification are characterized in that the agent additionally includes at least one anionic surfactant. Preferred anionic surfactants are fatty acids, alkyl sulfates, alkyl ether sulfates and ether carboxylic acids with 10 to 20 carbon atoms in the alkyl group and up to 16 glycol ether groups in the molecule. The anionic surfactants are used in an amount of from 0.1 to 45 wt. %, preferably from 1 to 30 wt. % and most particularly preferably from 1 to 15 wt. %, relative to the total amount of the ready-to-use agent.

Agents that are preferred according to the present specification are characterized in that the agent additionally includes at least one zwitterionic surfactant. Preferred zwitterionic surfactants are betaines, N-alkyl-N,N-dimethylammonium glycinates, N-acyl aminopropyl-N,N-dimethylammonium glycinates, and 2-alkyl-3-carboxymethyl-3-hydroxyethyl imidazolines. A preferred zwitterionic surfactant is known under the INCI name Cocamidopropyl Betaine.

Agents that are preferred according to the present specification are characterized in that the agent additionally includes at least one amphoteric surfactant. Preferred amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids. Particularly preferred amphoteric surfactants are N-cocoalkyl aminopropionate, cocoacylaminoethyl aminopropionate and $C_{12}$-$C_{18}$ acyl sarcosine.

It has moreover proved advantageous for the agents to include further, non-ionogenic interfacially-active substances. Preferred non-ionic surfactants are alkyl polyglycosides as well as alkylene oxide addition products with fatty alcohols and fatty acids, each including 2 to 30 mol of ethylene oxide per mol of fatty alcohol or fatty acid. Preparations having outstanding properties are likewise obtained if they include fatty acid esters of ethoxylated glycerol as non-ionic surfactants.

The non-ionic, zwitterionic or amphoteric surfactants are used in an amount of from 0.1 to 45 wt. %, preferably from 1 to 30 wt. % and most particularly preferably from 1 to 15 wt. %, relative to the total amount of the ready-to-use agent.

Agents that are suitable according to the present specification may also include cationic surfactants of the quaternary ammonium, esterquat and amidoamine types. Preferred quaternary ammonium compounds are ammonium halides and the imidazolium compounds known under the INCI names Quaternium-27 and Quaternium-83. Further cationic surfactants which may be used according to the present specification are the quaternized protein hydrolysates. A compound from the amidoamines that is particularly suitable according to the present specification is stearamidopropyl dimethylamine, which is commercially available under the name Tegoamid® S 18. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. The cationic surfactants are preferably included in the agents used according to the present specification in an amount of from 0.05 to 10 wt. %, relative to the total agent.

The ready-to-use coloring agents may include further auxiliary substances and additives. It has proved advantageous if the agents include at least one thickening agent. There are no restrictions in principle regarding these thickening agents. Both organic and also purely inorganic thickening agents may be used.

Suitable thickening agents are
anionic polymers,
cationic, synthetic polymers;
naturally occurring thickening agents, such as non-ionic guar gums, scleroglucan gums or gum arabic, ghatti gum, karaya gum, tragacanth gum, carrageen gum, carob seed meal, pectins, starch fractions and derivatives such as amylose, amylopectin and dextrins, as well as non-ionic cellulose derivatives, such as for example methyl cellulose and hydroxyalkyl celluloses;

non-ionic, fully synthetic polymers, such as polyvinyl alcohol or polyvinylpyrrolidone; as well as inorganic thickening agents, in particular phyllosilicates such as for example bentonite, particularly smectites, such as montmorillonite or hectorite.

Coloring processes on keratin fibers conventionally take place in an alkaline environment. In order to protect the keratin fibers and also the skin as far as possible, it is not desirable to establish too high a pH, however. The pH of the agents according to the present specification may therefore be between 3 and 11. It is preferable for the pH of the ready-to-use agent to be between 5 and 11, in particular between 5 and 8. The pH values within the meaning of the present specification are pH values measured at a temperature of 22 degrees Celsius (° C.).

The alkalizing agents which may be used according to the present specification to establish the preferred pH may be selected from the group formed from ammonia, alkanolamines, basic amino acids, as well as inorganic alkalizing agents such as alkaline-earth/alkali metal hydroxides, alkaline-earth/alkali metal metasilicates, alkaline-earth/alkali metal phosphates and alkaline-earth/alkali metal hydrogen phosphates. Preferred inorganic alkalizing agents are magnesium carbonate, sodium hydroxide, potassium hydroxide, sodium silicate and sodium metasilicate. Organic alkalizing agents that may be used according to the present specification are preferably selected from monoethanolamine, 2-amino-2-methylpropanol and triethanolamine. The basic amino acids that may be used as the alkalizing agent according to the present specification are preferably selected from the group formed from arginine, lysine, ornithine and histidine, particularly preferably arginine. In the context of the investigations leading to the agents of the present disclosure it has however been found that preferred agents according to the present specification are furthermore characterized in that they additionally include an organic alkalizing agent. One example of the first subject matter of the present specification is characterized in that the agent additionally includes at least one alkalizing agent which is selected from the group formed from ammonia, alkanolamines and basic amino acids, in particular from ammonia, monoethanolamine and arginine or the acceptable salts thereof.

It has furthermore proved advantageous for the coloring agents, particularly if they additionally include hydrogen peroxide, to include at least one stabilizer or complexing agent. Particularly preferred stabilizers are phenacetin, alkali benzoates (sodium benzoate) and salicylic acid. All known complexing agents may also be used. Preferred complexing agents according to the present specification are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

The agents according to the present specification may also include further active ingredients, auxiliary substances and additives, such as for example non-ionic polymers, such as vinylpyrrolidone/vinyl acrylate copolymers, polyvinylpyrrolidone, vinylpyirolidinone/vinyl acetate copolymers, polyethylene glycols and polysiloxanes; additional silicones such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidone copolymers quaternized with diethyl sulfate, vinylpyrrolidone-imidazolinium-methochloride copolymers and quaternized polyvinyl alcohol; zwitterionic and amphoteric polymers; structuring agents such as glucose, maleic acid and lactic acid, hair-conditioning compounds such as phospholipids, for example lecithin and cephalins.

The person skilled in the art will select these further substances in accordance with the desired properties of the agents. With regard to further optional components and to the amounts of these components used, reference is expressly made to the relevant manuals, for example Kh. Schrader, Grundlagen and Rezepturen der Kosmetika [Fundamentals and formulations of cosmetics], $2^{nd}$ Edition, Hüthig Buch Verlag, Heidelberg, 1989. The additional active ingredients and auxiliary substances are used in the agents according to the present specification preferably in amounts of from 0.0001 to 25 wt. % in each case, in particular from 0.0005 to 15 wt. %, relative to the total weight of the application mixture.

A method for coloring keratinic fibers, in particular human hair, which is characterized in that an agent of the first subject matter of the present specification is applied to the keratin-containing fibers, left on the fibers for from 5 to 60 minutes and then rinsed out again with water or washed out with a shampoo, is suitable in particular for the application of the agents according to the present specification. The contact time of the ready-to-use coloring agents is preferably from 5 to 45 minutes, in particular from 10 to 40 minutes, particularly preferably from 15 to 35 minutes. During the contact time of the agent on the fibers, it may be advantageous to support the lightening process by supplying heat. Heat may be supplied both from an external heat source, such as for example hot air from a hot air blower, and also, in particular if the hair lightening process is taking place on a living test subject, from the body temperature of the test subject. In the latter case the section to be lightened is conventionally covered with a hood. A contact phase at room temperature is likewise in accordance with the present specification. In particular, the temperature during the contact time is between 20° C. and 40° C., in particular between 25° C. and 38° C. After the end of the contact time the remaining coloring preparation is rinsed out of the hair with water or a cleaning agent. Commercial shampoo may be used in particular as the cleaning agent, wherein in particular if the lightening agent has a carrier having a high surfactant content, the cleaning agent may be dispensed with and the rinsing process may take place with water.

The agents according to the present specification may be formulated as one-component agents (coloring and lightening agent) or as multi-component agents such as two-component agents or three-component agents, and used accordingly. A separation into multi-component systems is useful in particular where incompatibilities between the ingredients are to be expected or of concern; in such systems, the agent to be used is prepared by the consumer immediately before use by mixing the components together.

If the agent according to the present specification includes both substantive dyes—as well as optionally additionally oxidation dye precursors—and oxidizing agents, they are conveniently packaged separately from one another in order to avoid a premature, undesired reaction and brought into contact only immediately before application.

A coloring and lightening method in which the coloring cream and the oxidizing agent are initially separate is therefore preferred. The present specification therefore also provides a method for coloring and lightening human hair, wherein a composition on an aqueous basis including hydrogen peroxide is mixed with an agent according to the present specification including at least one compound of formula (I) to form a homogeneous composition, and this is applied to the hair. The fatty acid diester of an alkanediol (b) may in this case be packaged with the hydrogen peroxide solution, with the compound of formula (I), or with both.

In a further example of the present specification, agents are therefore preferred which are characterized in that they are produced immediately before application by mixing at least two preparations, wherein the at least two preparations are provided in at least two separately packaged containers, and wherein one container contains an agent (A), which includes in a cosmetic carrier at least one cationic anthraquinone dye of formula (I), optionally including oxidation dye precursors as well, and a further container contains an oxidizing agent preparation (B) including at least one oxidizing agent. The fatty acid diester of an alkanediol (b) may in this case be packaged together with the cationic anthraquinone dye of formula (I) in container A, together with the oxidizing agent preparation in container (B), or both.

The formulation of a combination of (a) compounds of the general formula (I) with at least one (b) fatty acid diester of an alkanediol is outstandingly suitable for producing intense colors with high brilliance, high shine and a low selectivity in conjunction with an outstanding wash fastness. The agents are likewise outstandingly suitable for minimizing or preventing the drying out of the scalp.

The present specification also provides the use of an agent of the first subject matter of the present specification to produce hair dyes having increased shine, an intense color result with improved fastness properties and/or reduced selectivity.

All that has been stated in respect of the agents according to the present specification applies with necessary alterations to further preferred examples of the methods and use according to the present specification.

EXAMPLES

The examples that follow indicate agents that were produced according to the present specification for the treatment of keratinous fibers. Unless otherwise indicated, the stated quantities are percentages by weight.

Formulation Example 1

| Description | wt. % |
|---|---|
| Polyquaternium-10 | 0.45 |
| Citric acid monohydrate | 0.70 |
| Timiron Super Silver | 0.20 |
| Cationic Blue 347 | 0.20 |
| Salicylic acid | 0.20 |
| Disodium cocoamphodiacetate | 7.00 |
| Sodium benzoate | 0.50 |
| Nicotinamide | 0.50 |
| Sodium pyrrolidone-2-carboxylate | 2.00 |
| Cutina HR | 1.00 |
| PEG-7 glyceryl cocoate | 0.50 |
| Sodium myreth sulfate (2 EO), 70% | 24.00 |
| NaOH, 50% | 0.15 |
| D-Panthenol, 75% | 0.50 |
| Euperlan PK 3000 AM | 2.60 |
| ProSina | 2.0 |
| Sericin H | 0.20 |
| Caramel syrup, 75% | 0.60 |
| Apricot kernel oil | 0.10 |
| PEG-40 hydrogenated castor oil | 0.60 |

-continued

| Description | wt. % |
|---|---|
| Sodium chloride | 0.20 |
| Antil 141 L | 1.00 |
| Hydrolyzed silk protein | 1.50 |
| Benzophenone-4 | 0.50 |
| Perfume | qs |
| Water | to 100 |

Recipe Constituents

| | |
|---|---|
| Cationic Blue 347 | 3-[(4-amino-9,10-dihydro-3-methyl-9,10-dioxo-1-anthracenyl)amino]-N,N,N-trimethyl-1-propanaminium methosulfate |
| Timiron Super Silver | INCI name: Mica, Titanium Dioxide (Merck KGaA) |
| Cutina HR | INCI name: Hydrogenated castor oil (BASF) |
| Euperlan PK 3000 AM | approx. 43% solid substance; INCI name: Aqua, Ethylene Glycol Distearate, Glycerin, Laureth-4, Cocamidopropyl Betaine, Formic Acid (BASF) |
| ProSina | INCI name: Aqua, hydrolyzed Keratin (Keratec/Croda) |
| Sericin H | INCI name: Sericin (Pentapharm) |
| Antil 141 L | approx. 40% active substance; INCI name: Propylene Glycol, PEG-55 Propylene Glycol Oleate (Goldschmidt/Evonik) |

The coloring formulations were applied to hair strands and allowed to act on the hair strands for 30 minutes at room temperature. Then the fibers were rinsed thoroughly with water and dried.

The treated fibers were characterized by intense colors with high shine, an outstanding wash fastness and a soft feel.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of the elements described in an exemplary embodiment without departing from the scope of the invention as set forth in the appended claims and their legal equivalents.

The invention claimed is:

1. An agent for coloring keratinic fibers comprising, in a cosmetic carrier,
(a) at least one compound of formula (I):

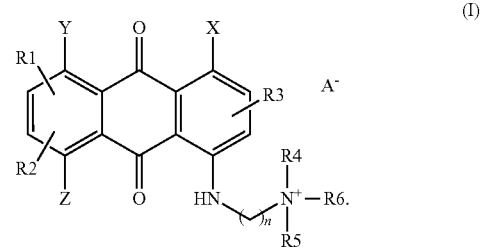

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:
R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;

n denotes an integer between 2 and 6 inclusive; and

A⁻ denotes a physiologically acceptable anion;

and (b) at least one fatty acid diester of an alkanediol.

2. The agent of claim 1, wherein the agent simultaneously lightens the keratinic fibers.

3. The agent of claim 1, wherein at least one of the radicals R1, R2 and R3 of formula (I) denotes a $C_1$-$C_6$ alkyl group.

4. The agent of claim 1, wherein X of formula (I) denotes an $NH_2$ group.

5. The agent of claim 1, wherein the compound of formula (I) is provided by a compound of formula (Ia)

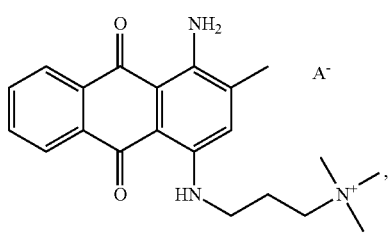

(Ia)

in which A⁻ denotes a physiologically acceptable anion.

6. The agent of claim 1, wherein the compound(s) according to formula (I) comprise an amount of from 0.0001 to 5 weight percent (wt. %), relative to the total weight of the agent.

7. The agent of claim 1, where the compound(s) according to formula (I) comprise an amount of from 0.005 to 3.5 wt. %, relative to the total weight of the agent.

8. The agent of claim 1, wherein the compound(s) according to formula (I) comprise an amount of from 0.01 to 2.5 wt. %, relative to the total weight of the agent.

9. The agent of claim 1, wherein the fatty acid diester of an alkanediol (b) is provided by a compound of formula (II):

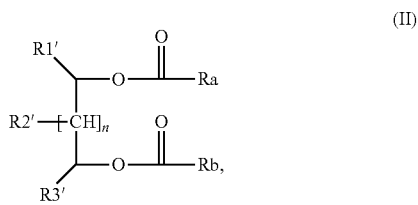

(II)

in which:
R1', R3' independently of one another, denote hydrogen, a $C_1$-$C_8$ alkyl group, an aryl group or a hydroxy-$C_1$-$C_6$ alkyl group, R2' denotes hydrogen, a $C_1$-$C_8$ alkyl group, an aryl group or a hydroxy-$C_1$-$C_6$ alkyl group, n denotes an integer from 0 to 8, and Ra, Rb independently of one another, denote a saturated or unsaturated, unbranched or branched, unsubstituted or substituted $C_7$-$C_{23}$ alkyl group.

10. The agent of claim 9, wherein Ra and Rb are selected from the group consisting of —$C_{13}H_{27}$ (F4), —$C_{15}H_{31}$ (F5), —$C_{17}H_{35}$ (F6), —$C_{19}H_{39}$ (F7) and the residues F12, F13, F16, F17, F21 and F22

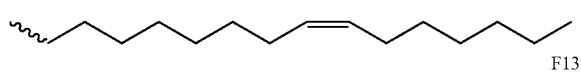

F12

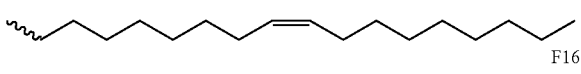

F13

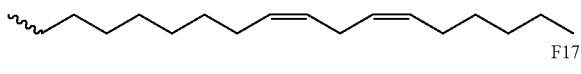

F16

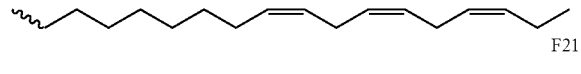

F17

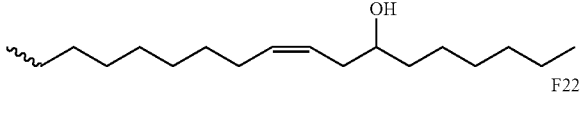

F21

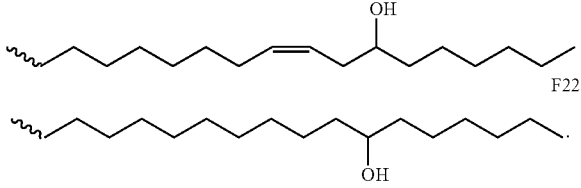

F22

11. The agent of claim 9, wherein the fatty acid diester of an alkanediol (b) is provided by a compound of formula (II):

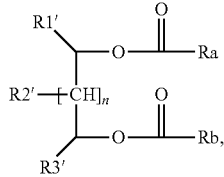

(II)

in which:
(a) Ra and Rb both denote a saturated, unbranched, unsubstituted $C_{14}$-$C_{20}$ alkyl group, and
(b) Ra and Rb are the same.

12. The agent claim 1, wherein the fatty acid diester of an alkanediol (b) is ethylene glycol distearate.

13. The agent of claim 1, wherein the fatty acid diester of an alkanediol (b) is propylene glycol distearate.

14. The agent of claim 1, wherein the fatty acid diester(s) of an alkanediol (b) comprise an amount of from 0.001 to 15 wt. %, relative to the total weight of the agent.

15. The agent of claim 1, wherein the fatty acid diester(s) of an alkanediol (b) comprise an amount of from 0.05 to 12 wt. %, relative to the total weight of the agent.

16. The agent of claim 1, further comprising hydrogen peroxide or a solid addition product thereof with organic or inorganic compounds.

17. The agent of claim 1, further comprising at least one anionic surfactant.

18. The agent of claim 1, further comprising at least one zwitterionic surfactant.

19. The agent of claim 1, further comprising at least one amphoteric surfactant.

20. A method of dyeing keratinic fibers to produce increased shine, an intense color result with improved fastness properties, or reduced selectivity, comprising:
(A) applying an agent for coloring, and optionally simultaneously lightening, keratinic fibers, comprising, in a cosmetic carrier,
(i) at least one compound of formula (I):

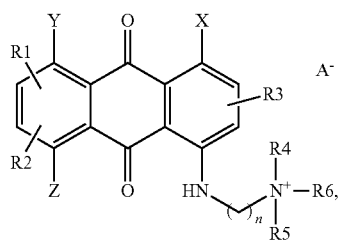

in which:

R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;

n denotes an integer between 2 and 6 inclusive; and $A^-$ denotes a physiologially acceptable anion;

and (ii) at least one fatty acid diester of an alkanediol; and (B) after a contact time, rinsing the agent from the keratinic fibers.

* * * * *